(12) United States Patent
Kiani

(10) Patent No.: US 8,637,094 B2
(45) Date of Patent: *Jan. 28, 2014

(54) COMPOSITION AND METHOD FOR TREATING VIRAL CONDITIONS

(76) Inventor: Iraj E. Kiani, Huntington Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/968,228

(22) Filed: Dec. 14, 2010

(65) Prior Publication Data

US 2011/0104302 A1  May 5, 2011

Related U.S. Application Data

(60) Continuation-in-part of application No. 12/541,856, filed on Aug. 14, 2009, now Pat. No. 7,850,998, which is a continuation-in-part of application No. 12/358,218, filed on Jan. 22, 2009, now Pat. No. 7,842,317, which is a division of application No. 11/880,029, filed on Jul. 18, 2007, now Pat. No. 7,700,137.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

| | | | |
|---|---|---|---|
| 4,012,508 A | 3/1977 | Burton | |
| 5,455,033 A | 10/1995 | Silverman et al. | |
| 5,785,972 A | 7/1998 | Tyler | |
| 6,231,848 B1 | 5/2001 | Breitenbach et al. | |
| 6,358,516 B1 | 3/2002 | Harod | |
| 6,593,371 B1 | 7/2003 | Staggs | |
| 6,899,903 B2 | 5/2005 | Quillin | |
| 6,946,490 B2 | 9/2005 | Squires | |
| 7,071,233 B2 | 7/2006 | Squires | |
| 7,087,250 B2 | 8/2006 | Marchioni | |
| 7,115,287 B2 | 10/2006 | Froggatt et al. | |
| 7,700,137 B1 | 4/2010 | Kiani | |
| 7,842,317 B2 | 11/2010 | Kiani | |
| 7,850,998 B2 | 12/2010 | Kiani | |
| 2003/0113388 A1 | 6/2003 | Phan | |
| 2004/0091556 A1 | 5/2004 | Tigunalt et al. | |
| 2004/0110738 A1 | 6/2004 | Gillis et al. | |
| 2004/0185123 A1 | 9/2004 | Mazzio | |
| 2005/0013854 A1 | 1/2005 | Mannino et al. | |
| 2005/0037034 A1 | 2/2005 | Rhoades | |
| 2006/0052438 A1 | 3/2006 | Ho et al. | |
| 2006/0073221 A1 | 4/2006 | Lam | |
| 2006/0182813 A1 | 8/2006 | Holladay | |
| 2006/0251731 A1 | 11/2006 | Marchioni | |
| 2007/0036834 A1 | 2/2007 | Pauletti et al. | |
| 2007/0059255 A1 | 3/2007 | Tichy et al. | |
| 2007/0092547 A1 | 4/2007 | Birnbaum et al. | |

FOREIGN PATENT DOCUMENTS

| | | |
|---|---|---|
| GB | 2311009 | 9/1997 |
| JP | 61205465 | 9/1986 |
| JP | 2004350505 | 12/2004 |
| WO | WO2006/109898 | 10/2006 |

OTHER PUBLICATIONS

Mayo Clinic; Tea Tree Oil (*Melaleuca alternifolia* [Maiden & Betche] Cheel, www.mayoclinic.com/health/tea-tree-oil/NS_patient_teatreeoil (Natural Standard Patient Monograph, 2007.
Banerji, P.; Intracranial Cysticercosis: An Effective Treatment with Alternative Medicines; In Vivo, Mar.-Apr. 2001, 15(2):181-4; www.ncbi.nlm.nih.gov (NCBI PubMed) (Abstract Only).
Preethi, KC, et al.; Anti-Tumour Activity of *Ruta graveolens* Extract; Asian Pac J. Cancer Prev. Jul.-Sep. 2006, 7(3):439-43; www.ncbi.nlm.nih.gov (NCBI PubMed) (Abstract Only).
Ivanova A., et al.; Antimicrobial and cytotoxic activity of *Ruta graveolens*; Fitoterapia, Jun. 2005,76(3-4):344-47; www.ncbi.nlm.nih.gov (NCBI PubMed) (Abstract Only).
Oliva A. et al.; Natural fungicides from *Ruta graveolens* L. leaves, including a new quinolone alkaloid; J. Agric. Food Chem., Feb. 12, 2003, 51(4):890-6; www.ncbi.nlm.nih.gov (NCBI PubMed) (Abstract Only).
Meepagala KM, et al.; Algicidal and antifungal compounds from the roots of *Ruta graveolens* and synthesis of their analogs; Phytochemistry, Nov. 2005, 66(22):2689-95, Epub Nov. 4, 2005; www.ncbi.nlm.nih.gov (NCBI PubMed) (Abstract Only).
Raghav, SK, et al.; Anti inflammatory effect of *Ruta graveolens* L. in murine macrophage cells; j. Ethnopharmacology, Mar. 8, 2006, 104(1-2):234-39 Epub Oct. 3, 2005; www.ncbi.nlm.nih.gov (NCBI PubMed) (Abstract Only).
Young, Lee W.; Transmittal of International Search Report and Written Opinion mailed on May 11, 2000 in Applicant's co-pending PCT International Application No. PCT/US2010/027680.
Ebrahimi et al.; "Efficacy of 10% silver nitrate solution in the treatment of common warts: a placebo-controlled, randomized, clinical trial." Int J Dermatol., 2007, vol. 46(2), pp. 215-217 (Abstract Only).
Zerrin, Unripe Fig Jam, GiveRecipe.com, Jun. 20, 2009, pp. 1-18, www.giverecipe.com/tag/skin-warts-treatment/.

*Primary Examiner* — Michael Meller
(74) *Attorney, Agent, or Firm* — Kelly W. Cunningham, Esq.; Cislo & Thomas LLP

(57) ABSTRACT

An antiviral composition and a method of treating viral conditions comprising colloidal silver, silver nitrate, or both, and an antiviral natural herb or a natural herb from the Rutaceae family, such as *Ruta graveolens*, Myrtaceae family, such as *Melaleuca alternifolia*, Cupressaceae family, such as *Thuja occidentalis*, and the Moraceae family, such as fig, or any combination thereof.

5 Claims, No Drawings

COMPOSITION AND METHOD FOR TREATING VIRAL CONDITIONS

CROSS-REFERENCE TO RELATED APPLICATION

This patent application is a continuation-in-part application of U.S. patent application Ser. No. 12/541,856 filed Aug. 14, 2009, now U.S. Pat. No. 7,850,998, which is a continuation-in-part patent application of U.S. patent application Ser. No. 12/358,218 filed Jan. 22, 2009, now U.S. Pat. No. 7,842,317, which is a divisional of U.S. patent application Ser. No. 11/880,029, filed Jul. 18, 2007, now U.S. Pat. No. 7,700,137, which applications are incorporated in their entirety here by this reference.

TECHNICAL FIELD

This invention relates to compositions and methods for treating viral conditions.

BACKGROUND ART

Viruses have long plagued the earth resulting in conditions ranging from simple to severe discomfort, such as that caused by warts, HPV, and herpes, to death such as that caused by HIV and cancer. Unlike bacterial and fungal infections, viral infections have proven difficult to treat, partly due to the fact that viral infections involve injection of the virus's genetic material into the host cell and partly because of the virus's ability to mutate.

Despite advances in technology and scientific research pathogens, such as viruses, bacteria, fungus, and other microorganisms, continue to cause disease, disorders, and dysfunctions. Current treatments suffer from inefficacy and/or undesirable side effects. Often times treatments that are effective for one patient are not effective for another. Thus, scientists and physicians are in continual pursuit of new treatments and drugs that are more effective, less toxic, and easily produced.

SUMMARY

The present invention is directed to an antiviral composition and a method for the treating viral infections comprising, among other things, colloidal silver, silver nitrate, or both, and one or more antiviral natural herbs such as *Ruta Graveolens; Melaleuca Alternifolia, Thuja Occidentalis*, and/or FIG.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The present invention is directed towards the prevention and treatment of a viral condition or disorder caused by a pathogen with a composition comprising a transition metal in colloidal form and one or more natural herbs. Diseases, disorders, or conditions caused by such pathogens include, without limitation, cancer, warts, herpes, genital herpes, and infections caused by the human papilloma virus.

One embodiment is an antiviral composition for treating a viral condition, comprising a therapeutically effective amount of a colloidal silver, silver nitrate, or both, and a therapeutically effective amount of an antiviral natural herb. Antiviral natural herbs defined herein include without limitation, *Echinacea, Allium sativum* (garlic), *Glycyrrhiza glabra* (licorice root), *Astragalus, Scutellaria baicalensis, Cinchona* bark, *Zingiber officinale* (ginger), grapefruit seed extract, *Lonicera japonica* (honeysuckle), *Olea europea* (olive leaf), *Sambucus nigra* (black elderberry), *Rudbeckia* (black-eyed Susan root), *Forsythia suspensa* (forsythia), *Isatis tinctora* (isatidis), *Lomatium dissecutim* (leptotaenia), and *Schizandra chinensis* (schizandra), *Croton lechleri* (dragon's blood), *Hydrastis Canadensis* (goldenseal), *Juniperus* (juniper), *Melissa officinalis* (lemon balm), *Lentinus edodes* (shiitake), and *Eucalyptus globules* (eucalyptus). These antiviral natural herbs produce their antiviral effects by reducing further spread of the infection and/or by boosting the immune system's response to the infection. The Applicant believes that such antiviral natural herbs themselves have very limited efficacy, if any, as an antiviral agent on their own. The administration of colloidal silver, silver nitrate, or both, in combination with an antiviral natural herb, however, appears to have greatly superior effects that improve the efficacy of the antiviral properties of the composition far beyond the effectiveness of either the colloidal silver, silver nitrate, or both, or the anti-viral natural herb.

The colloidal silver, silver nitrate, or both, may be present in an amount of anywhere from approximately 1% to approximately 75% by weight of the total composition. In another embodiment, the amount of colloidal silver, silver nitrate, or both, may be approximately 1% to approximately 50% of the composition by weight. In more typical embodiments, the amount of colloidal silver, silver nitrate, or both, may be approximately 1% to approximately 25% of the composition by weight.

In certain embodiments, the antiviral composition comprises colloidal silver, silver nitrate, or both, and other natural herbs. A natural herb as used in this application includes, among other things, FIG. Fig may include ripe fig, unripe fig, and fig at any other stage of ripeness or maturity. The natural herb may be from, for example, without limitation, the evergreen shrubs of the Rutaceae family, for example the *Ruta* genus; the Myrtaceae family, and more specifically, the *Melaleuca* genus for example. Alternatively, or in combination with the forgoing, the natural herb could also be derived from the woody trees, shrubs, and vines of the Moraceae family, for example the *Ficus* genus; the evergreen coniferous tree in the cypress family Cupressaceae, for example the *Thuja* genus; or any combination thereof. Other examples of the antiviral herb include *Ruta Graveolens* of the Rutaceae family, *Melaleuca Alternifolia*, also known as Narrow-leaved Paperbark, Narrow-leaved Tea-tree, Narrow-leaved Ti-tree, or Snow-in-summer from the Myrtaceae family; *Thuja Occidentalis* from the Cupressaceae family; or figs from the Moraceae family, or any combination thereof. Furthermore, in some embodiments, the composition may further comprise red or fig vinegar, or the composition may be fermented.

In certain embodiments, this invention is directed towards a method of treating a viral condition, comprising administering a therapeutically effective amount of a colloidal silver, silver nitrate, or both, and administering a therapeutically effective amount of an anti-viral natural herb, whereby the viral condition is ameliorated. In certain embodiments, a viral condition may be treated by administering a therapeutically effective amount of colloidal silver, silver nitrate, or both, and a therapeutically effective amount of a natural herb.

The administration step may be any method of drug delivery, for example, topical application, oral administration, patch application, rinse solution, subcutaneous injection, or the like. Most typically, the composition is administered by topical application. Topical application includes any application resulting in administration of the composition to the surface of the skin. Generally, one or two drops of the composition are sufficient for small treatment areas of 1 millimeter diameter or less. Preferably, a sufficient amount of the composition should be applied such that any sores, lesions, neoplasm, or tumors are sufficiently covered.

In embodiments administered topically, the composition may further comprise a cream, gel, ointment, tablet, capsule, and the like to prolong the contact between the active ingredients and the point of treatment on the skin.

In many embodiments, the composition of the present invention may be administered once every other day. In other embodiments, the composition may be administered once per week or more. In still other embodiments, the composition may be administered once or more a day.

The anti-viral herb or the natural herb may be present in amounts between approximately 25% to approximately 99% by weight by weight of total composition. Preferably, the anti-viral natural herb or the natural herb is present in amounts between approximately 50% to approximately 99% by weight of total composition. More preferably, the antiviral natural herb or the natural herb is present in amounts between approximately 75% to approximately 99% by weight of total composition.

EXAMPLES

A male subject suffered from plantars wart on the bottom of his foot for thirty years. Multiple attempts to treat the wart were unsuccessful. The subject was treated with a composition comprising 10% by weight of total composition of 2000 ppm colloidal silver, silver nitrate, or both, and 90% by weight of total composition of a combination of tea tree, *Ruta graveolens, Thuja occidentalis*, and FIG. The subject was treated once per week for three weeks. After three weeks of treatment, the plantar's wart had entirely disappeared. In other treatments, positive results were also seen with other concentrations of colloidal silver, silver nitrate, or both, including 10% by weight of 500 ppm.

While the present invention has been described in regard to particular embodiments, it is recognized that additional variations of the present invention may be devised without departing from the inventive concept.

What is claimed is:

1. An antiviral composition, wherein the viral condition comprises a disease caused by human papilloma virus, and wherein the composition comprises:
   (a) a therapeutically effective amount of colloidal silver; and
   (b) a therapeutically effective amount of fig.

2. The antiviral composition of claim 1, wherein the colloidal silver is present in an amount between approximately 1% to approximately 75% by weight of the total antiviral composition.

3. The antiviral composition of claim 1, wherein the fig is present in an amount between approximately 25% and approximately 99% by weight of the total antiviral composition.

4. The antiviral composition of claim 1, wherein the colloidal silver is present in an amount between approximately 1% to approximately 25% by weight of the total antiviral composition.

5. The antiviral composition of claim 1, wherein the fig is present in an amount between approximately 75% and approximately 99% by weight of the total antiviral composition.

\* \* \* \* \*